(12) United States Patent
Luntz et al.

(10) Patent No.: US 10,772,699 B2
(45) Date of Patent: Sep. 15, 2020

(54) MECHANOTRANSDUCTIVE BOWEL EXTENDER DEVICE HAVING LOCAL DELIVERY OF MEDICALLY RELEVANT LIQUIDS

(71) Applicant: THE REGENTS OF THE UNIVERSITY OF MICHIGAN, Ann Arbor, MI (US)

(72) Inventors: Jonathan E. Luntz, Ann Arbor, MI (US); Meredith Barrett, Ann Arbor, MI (US); Diann Erbschloe Brei, Milford, MI (US); Brent Utter, Easton, PA (US); Farokh R. Demehri, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 84 days.

(21) Appl. No.: 16/096,321

(22) PCT Filed: Apr. 27, 2017

(86) PCT No.: PCT/US2017/029817
§ 371 (c)(1),
(2) Date: Oct. 25, 2018

(87) PCT Pub. No.: WO2017/189835
PCT Pub. Date: Nov. 2, 2017

(65) Prior Publication Data
US 2019/0125474 A1 May 2, 2019

Related U.S. Application Data

(60) Provisional application No. 62/328,703, filed on Apr. 28, 2016.

(51) Int. Cl.
*A61B 90/00* (2016.01)
*A61M 29/02* (2006.01)
(Continued)

(52) U.S. Cl.
CPC .............. *A61B 90/02* (2016.02); *A61B 17/00* (2013.01); *A61B 17/12045* (2013.01);
(Continued)

(58) Field of Classification Search
CPC ... A61B 90/02; A61B 17/00; A61B 17/12045; A61B 17/12099; A61M 25/10
(Continued)

(56) References Cited

U.S. PATENT DOCUMENTS 6,939,291 B2    9/2005  Phee Soo Jay et al.
2004/0073082 A1  4/2004  Phee Soo Jay et al.
(Continued)

FOREIGN PATENT DOCUMENTS

KR   10-2003-0078951 A    10/2003
WO       03033045 A2       4/2003

OTHER PUBLICATIONS

International Search Report and Written Opinion issued in PCT/US2017/029817, dated Aug. 8, 2017; ISA/KR.
(Continued)

*Primary Examiner* — John P Lacyk
(74) *Attorney, Agent, or Firm* — Harness, Dickey & Pierce, P.L.C.

(57) ABSTRACT

A mechanotransductive bowel extender device that can be used to correct short bowel syndrome by applying tension to the bowel tissue which, via the process of mechanotransduction, grows in length in response to the applied tension. Such a device is placed within the small bowel and applies tension over a period of several days or weeks by attaching to the lumen of the bowel at two different locations and
(Continued)

moving those two points apart, stretching the tissue between. The extender device further capable of localized application and/or evacuation of medically relevant liquid and other material within the bowel.

19 Claims, 4 Drawing Sheets

(51) Int. Cl.
    *A61M 25/10*     (2013.01)
    *A61B 17/12*     (2006.01)
    *A61B 17/00*     (2006.01)
    *A61M 19/00*     (2006.01)
    *A61M 31/00*     (2006.01)

(52) U.S. Cl.
    CPC .. *A61B 17/12099* (2013.01); *A61B 17/12136* (2013.01); *A61M 19/00* (2013.01); *A61M 25/10* (2013.01); *A61M 25/1011* (2013.01); *A61M 29/02* (2013.01); *A61M 31/005* (2013.01); *A61B 2017/00539* (2013.01); *A61B 2017/00818* (2013.01); *A61B 2017/12127* (2013.01); *A61M 2025/1015* (2013.01); *A61M 2025/1052* (2013.01); *A61M 2210/1064* (2013.01)

(58) Field of Classification Search
    USPC .......................................................... 600/37
    See application file for complete search history.

(56) References Cited

U.S. PATENT DOCUMENTS

| | | |
|---|---|---|
| 2006/0271162 A1 | 11/2006 | Vito et al. |
| 2009/0240339 A1 | 9/2009 | Teitelbaum et al. |
| 2012/0022572 A1 | 1/2012 | Braun et al. |
| 2012/0083820 A1 | 4/2012 | Carman et al. |
| 2015/0335331 A1 | 11/2015 | Utter et al. |

OTHER PUBLICATIONS

European Search Report issued in European Application No. 17790422.4 dated Oct. 29, 2019.

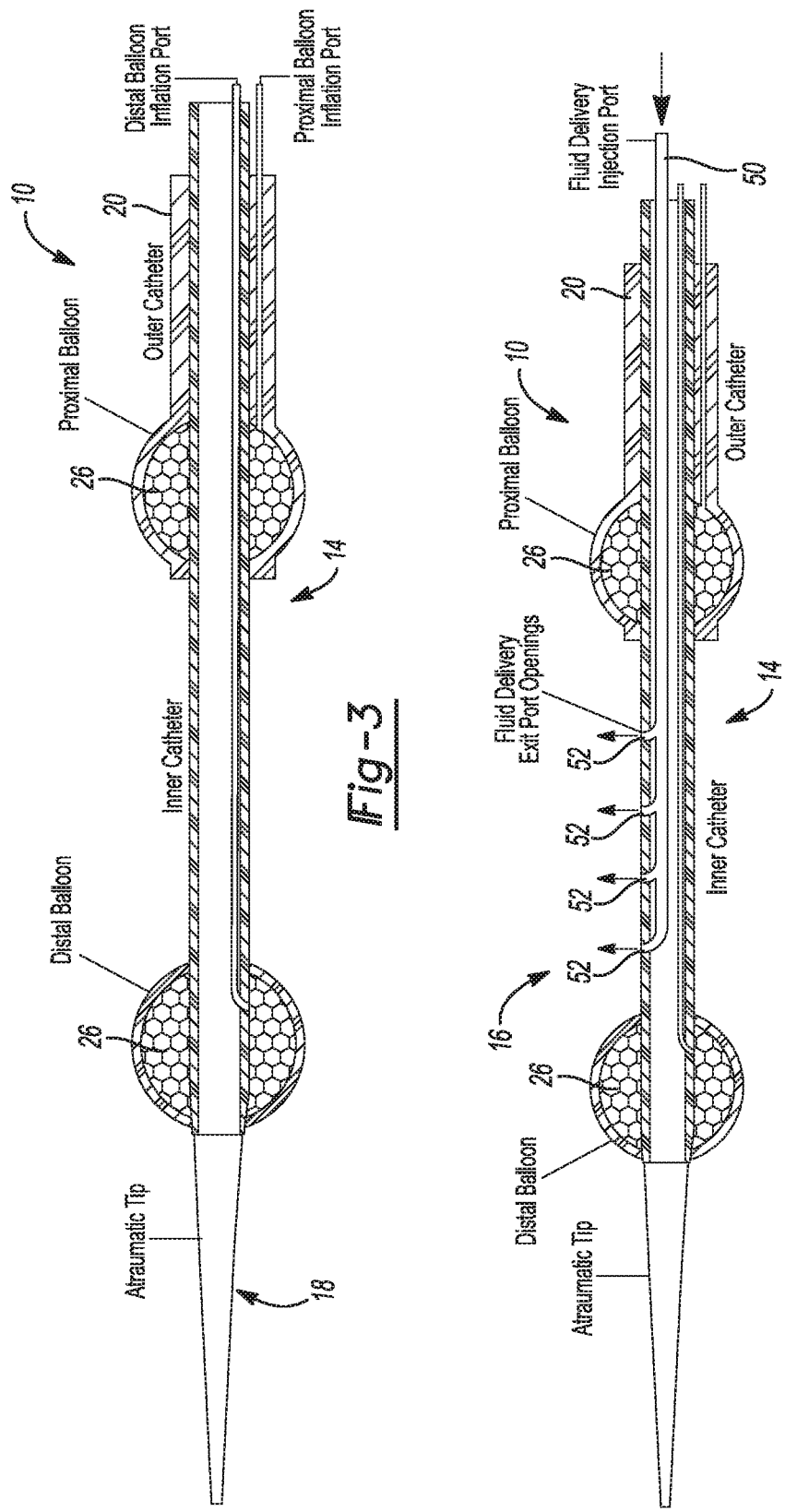

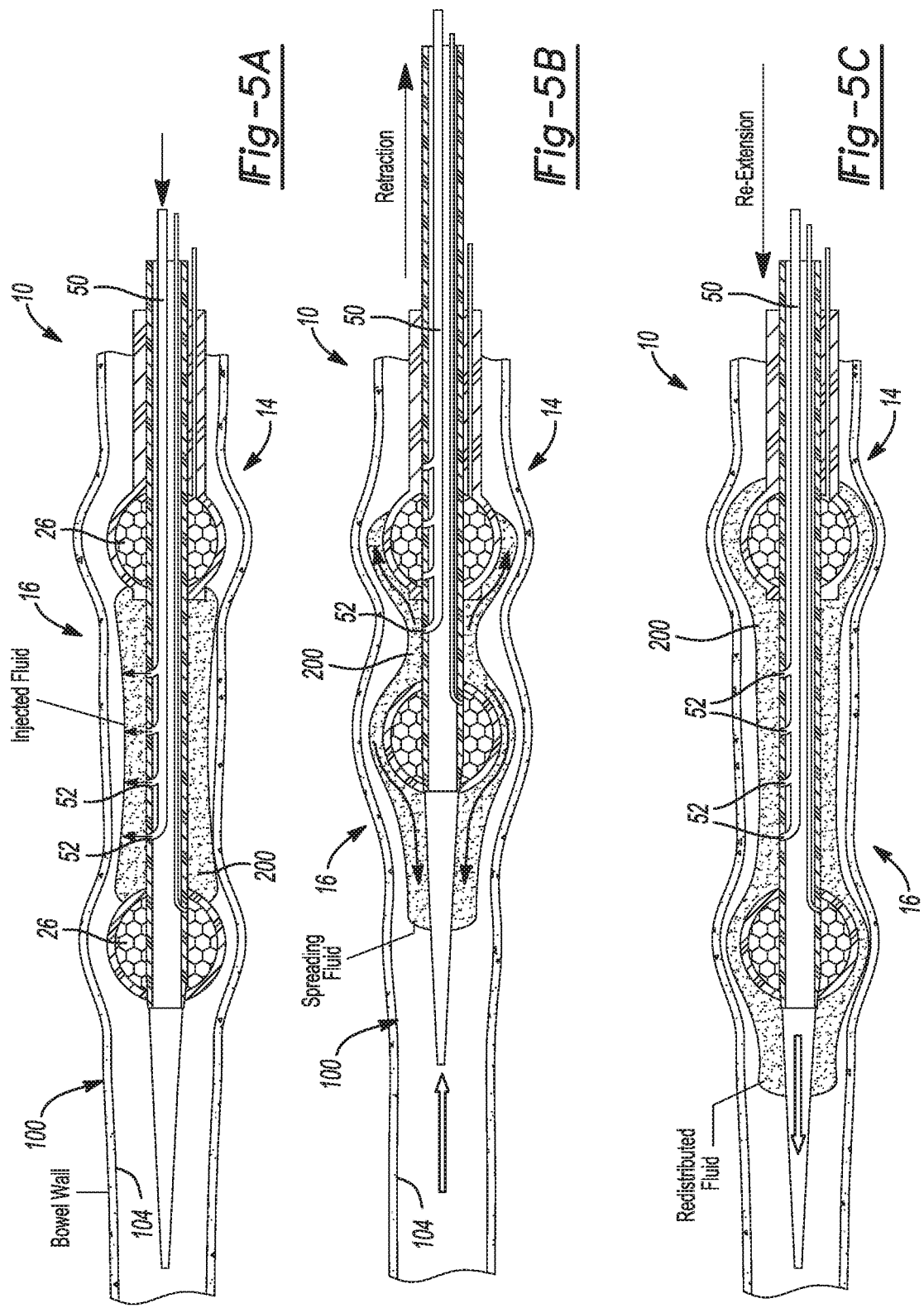

MECHANOTRANSDUCTIVE BOWEL EXTENDER DEVICE HAVING LOCAL DELIVERY OF MEDICALLY RELEVANT LIQUIDS

CROSS-REFERENCE TO RELATED APPLICATIONS

This application is a U.S. National Phase Application under 35 U.S.C. 371 of International Application No. PCT/US2017/029817 filed on Apr. 27, 2017, which claims the benefit of U.S. Provisional Application No. 62/328,703, filed on Apr. 28, 2016. The entire disclosures of the above applications are incorporated herein by reference.

FIELD

The present disclosure relates to a mechanotransductive bowel extender device and, more particularly, relates to a mechanotransductive bowel extender device employing local delivery of medically relevant liquids.

BACKGROUND AND SUMMARY

This section provides background information related to the present disclosure which is not necessarily prior art. This section also provides a general summary of the disclosure, and is not a comprehensive disclosure of its full scope or all of its features.

Short bowel syndrome (SBS) is a condition in which congenital, infectious, or traumatic injuries result in loss of bowel length and this decreased intestinal surface area is unable to absorb sufficient nutrients to sustain life. Parenteral nutrition (PN), in which calories and nutrients are delivered intravenously, is life sustaining but associated with many complications including infection, liver disease, and even death. Current treatments for SBS are inadequate with cure rates reaching only 30-40%.

The principles of the present teachings provide a mechanotransductive bowel extender device that can be used to correct short bowel syndrome by applying tension to the bowel tissue which, via the process of mechanotransduction, grows in length in response to the applied tension. Such a device is placed within the small bowel and applies tension over a period of several days or weeks by attaching to the lumen of the bowel at two different locations and moving those two points apart, thereby stretching the tissue.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3 illustrates a schematic of a manually actuated catheter-style bowel extension device with fenestrated mesh balloon attachments and atraumatic tip according to the principles of the present teachings.

FIG. 4 illustrates fluid delivery features added to a catheter-style bowel extender device enable the application of medically relevant liquids to the bowel tissue surrounding the device according to the principles of the present teachings.

FIGS. 5A-5C illustrates medically relevant liquid more evenly distributed along the bowel tissue via reciprocating motion of the bowel extender device according to the principles of the present teachings.

Corresponding reference numerals indicate corresponding parts throughout the several views of the drawings.

DETAILED DESCRIPTION

Figure 1:
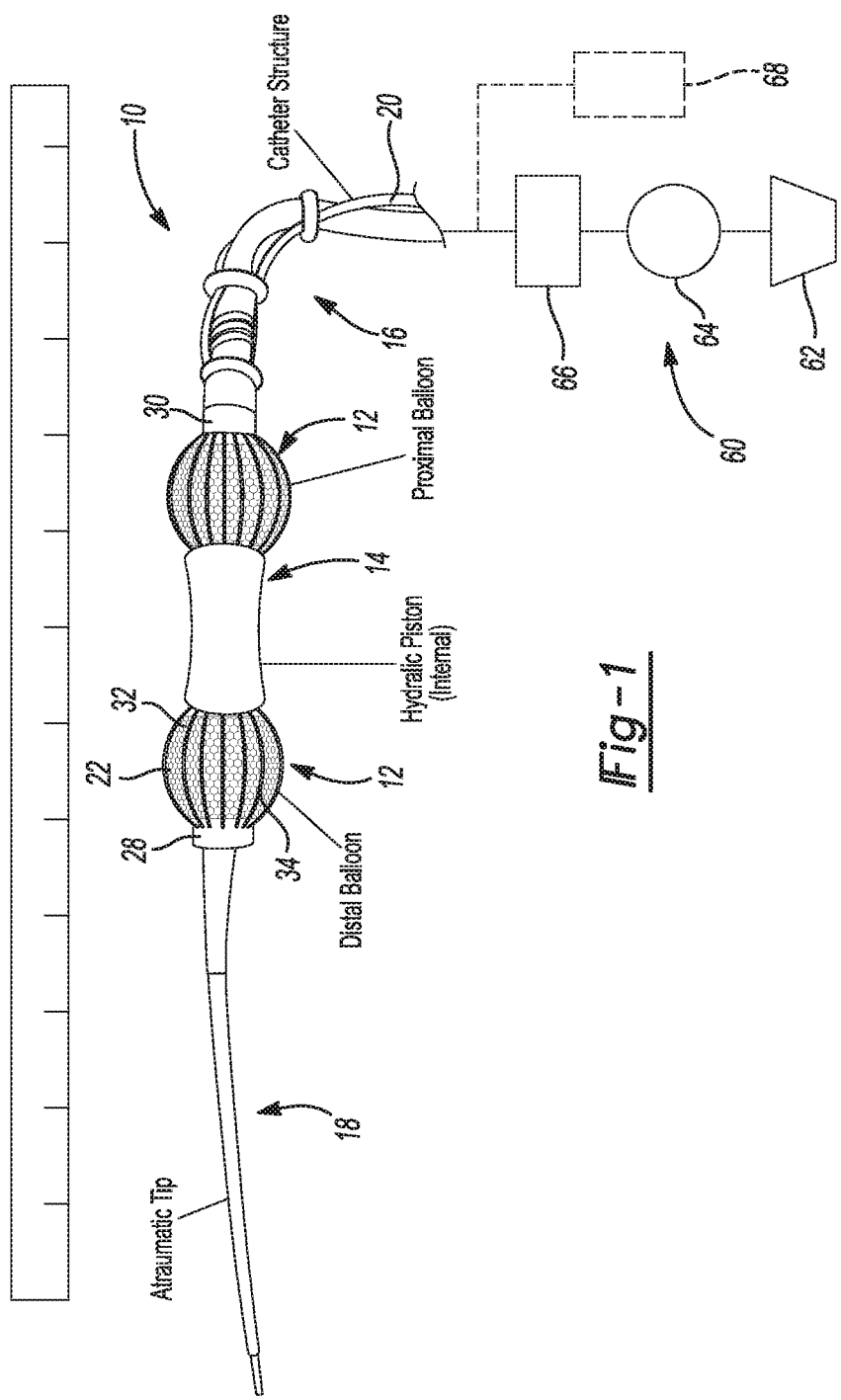
FIG. 1 illustrates the hydraulic actuated bowel extender device with fenestrated mesh balloons and atraumatic tip according to the principles of the present teachings.

Example embodiments will now be described more fully with reference to the accompanying drawings. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms.

These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

According to the principles of the present teachings, as illustrated in FIGS. 1-5C, a mechanotransductive bowel extender device 10 is disclosed that can be used to correct short bowel syndrome by applying tension to the bowel tissue 100 (FIGS. 5A-5C) which, via the process of mechanotransduction, grows in length in response to the applied tension. Bowel extender device 10 is placed within the small bowel and applies tension over a period of time, typically on the order of several days or weeks, by attaching to the bowel lumen 100 at two different locations (generally denoted at regions X and Y and moving those two points apart, thereby stretching the bowel tissue 100.

With particular reference to FIG. 1, in some embodiments, bowel extender device 10 is particular configured to permit the delivery of a medically relevant liquid at a treatment location via bowel extender device 10. In some embodiments, bowel extender device 10 can comprise a pair of engagement features 12, an elongation system 14, a medically relevant liquid delivery system 16, an optional atraumatic tip 18, and catheter structure 20. Generally, bowel extender device 10 is sized and configured to be inserted within the bowel 100 of a mammal, typically human being, for treatment of short bowel syndrome via mechanotransduction.

In some embodiments, engagement features 12 can comprise a fenestrated attachment system 22 each spaced apart from the other to define a distance therebetween that is variable in response to actuation of elongation system 14 (see FIGS. 5B and 5C). More particularly, upon actuation of elongation system 14, a driving force is imparted between the pair of fenestrated mesh textured balloon attachments 22 that imparts a tensile force upon the bowel to encourage bowel growth. In some embodiments, balloon attachment 22 is a toroidal structure that is fixed outside the catheter structure.

Fenestrated Attachment System

In some embodiments, to facilitate the selective attachment and detachment of bowel extender device 10 from the bowel lumen or other hollow member 100, a fenestrated attachment system 22, such as an endoluminal balloon attachment mechanism, is provided that employs a fenestrated decoupling system 24. The fenestrated attachment system 22 is placed within the bowel lumen or other hollow organ member 100 and is capable of radially expanding, thereby coupling with the inner luminal surface 104 of the bowel or other interior surface 104 of the hollow member 100, to allow transfer of longitudinal tensile loads to the bowel wall or hollow member 100 and/or permit translation therethrough.

In some embodiments, fenestrated attachment system 22 comprises an expanding device 26 (e.g. balloon) disposed on at least one end 28, 30. However, in most embodiments, a pair of expanding devices or balloons 26 will be used. In some embodiments, expanding device 26 is enlargeable between a deflated position (first size position) and an inflated position (second size position), whereby the inflated position is sufficiently large to permit mechanical engagement with the interior surface 104 of the hollow member 100 (i.e. bowel lumen). It should be understood that in some embodiments, the size of the inflated position must be sufficiently large to further accommodate any resultant enlargement of the hollow member in response to application of the inflation force. Likewise, it should be understood that in some embodiments, the size of the deflated position must be sufficiently smaller to permit disengagement of fenestrated attachment system 22 from the interior surface 104 of hollow member 100, at least when used in conjunction with fenestrated decoupling system 24.

In some embodiments, fenestrated attachment system 22 further comprises a friction enhancement or texture 32. In some embodiments, friction enhancement 32 can comprise application of an abrasive texture generally surrounding expanding device 26 that is capable of expanding during inflation of expanding device 26 and retracting during deflation of expanding device 26. In some embodiments, it has been found that an open-cell matrix, such as a 3M, Scotch-Brite Dobie, is useful. In some embodiments, friction enhancement 32 can comprise a fabric material structure surrounding expanding device 26. The fabric material structure can include one or more fibers knitted into a series of interlocked loops such that the knitted fabric can expand and contract along with expanding device 26. The loops can engage the interior surface 104 of the hollow member 100. In some embodiments, the fibers can include a flat ribbon such that the edges of the flat ribbon engage with the interior surface of the hollow member. In some embodiments, the friction enhancement 32 can include a plurality of bristles fixed to expanding device 26 engageable with the interior surface of the hollow member. In some embodiments, the friction enhancement 32 can include a plurality of loops fixed to the expanding member which engage the interior surface of the hollow member. Moreover, in some embodiments, the friction enhancement 32 comprises a plurality of scales, suction cups, and/or ridges fixed to the expanding device 26 which engage with the interior surface of the hollow member.

However, it was found that in some applications, friction enhancement 32 may not reliably disengage from interior surface 104 of hollow member 100 even after expanding device 26 is deflated and friction enhancement 32 is in the retracted position. Failure to disengage from interior surface 104 may inhibit further insertion, removal, and/or purposeful repositioning of the device. Accordingly, fenestrated decoupling system 24 can be employed about friction enhancement 32 to encourage disengagement of friction enhancement 32 from interior surface 104 upon deflation of expanding device 26. In some embodiments, fenestrated decoupling system 24 can comprise a plurality of bands 34 being disposed longitudinally along friction enhancement 32 at radial positions radially thereabout. In some embodiments, the plurality of bands 34 are comprises of elastic bands, which can be made of a monofilament material. The plurality of bands 34 can be retained by a pair of ring members disposed at opposing sides of fenestrated attachment system 22 that permit the plurality of bands 34 to pass there over and be captured and retained within fenestrated attachment system 22.

During operation, in some embodiments, fenestrated decoupling system 24 is operable to expand to accommodate inflation of expanding device 26 and, by association, enlarge friction enhancement 32, thereby permitting friction enhancement 32 to engage the interior surface 104 of hollow member 100. Once friction enhancement 32 is operably engaged with interior surface 104, elongation system 14 of bowel extender device 10 can be actuated. Conversely, once actuation is complete, expanding device 26 can be deflated and, by association, retract friction enhancement 32. This permits friction enhancement 32 to retract. The plurality of bands 34 of fenestrated decoupling system 24 can similarly retract. Retraction of friction enhancement 32 to a size smaller than retraction of the plurality of bands 34 of fenestrated decoupling system 24 can permit the plurality of bands 34 to disengage interior surface 104 of hollow member 100 from friction enhancement 32, thereby permitting insertion, removal, and purposeful repositioning of the device.

In some embodiments, device 10 includes a catheter structure extending from device 10 situated within the bowel to the exterior of the body through either a natural or surgically created body orifice to the outside of the body. This catheter enables the delivery of air and or fluids to inflate expanding device 26 and actuate elongation system 14. When inflated, expanding devices 26 contact the inner lumen 104 of the bowel 100, temporarily attaching to the bowel 100. The elongation system 14, such as a hydraulic piston, is then extended, separating expanding devices 26 (e.g. increasing a distance therebetween), thereby applying tension to the bowel. The device 10 is left in this position for a period of several hours or days over which the bowel tissue responds to the applied tension by growing, gradually relieving the tension. The balloons 26 are then deflated, detaching from the newly grown bowel, and the hydraulic piston 14 is retracted, bringing the device 10 back to its initial configuration. This process can be repeated to continually grow additional bowel.

Elongation System

Figure 2:
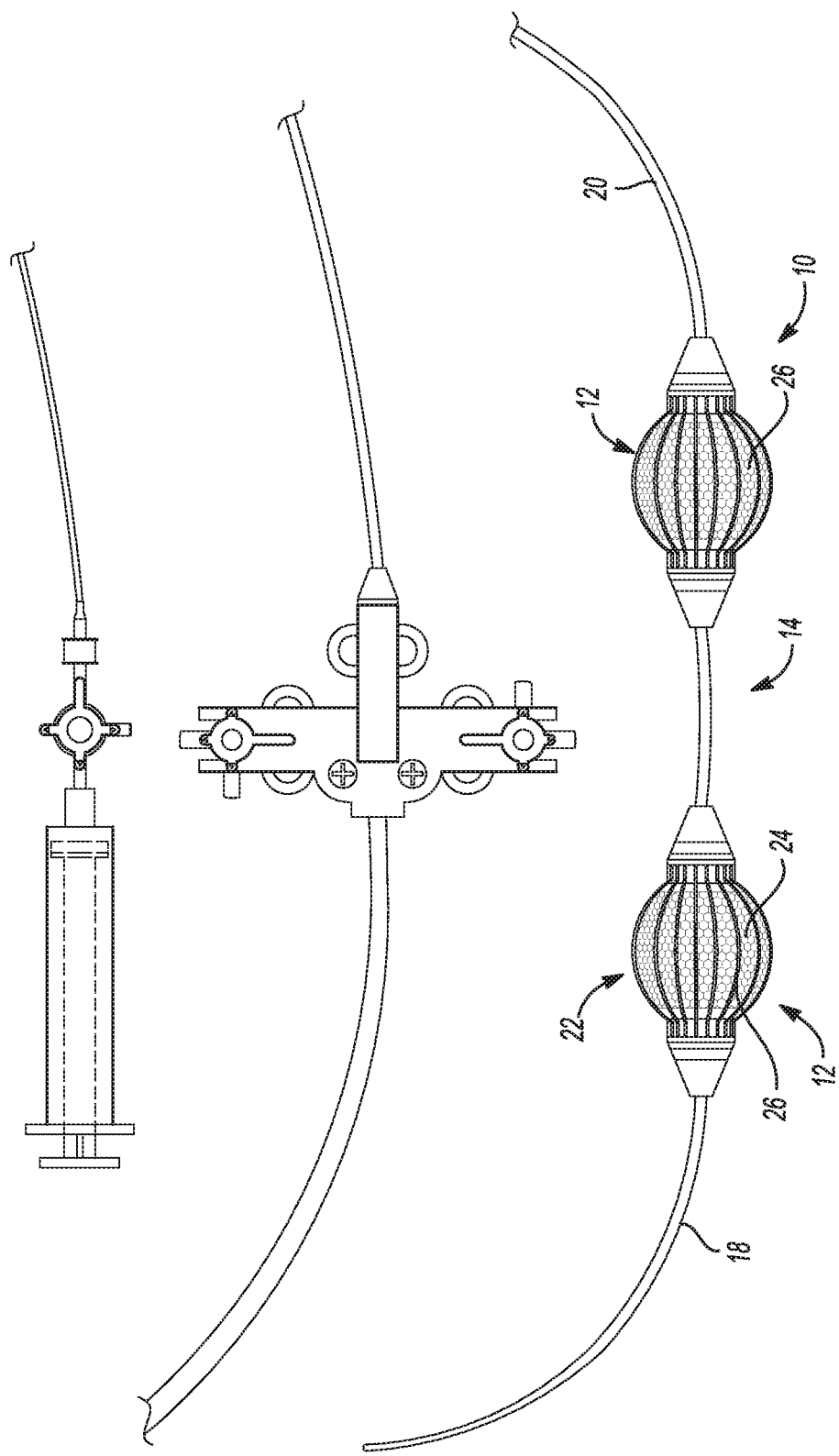
FIG. 2 illustrates a manually actuated catheter-style bowel extension device with fenestrated mesh balloon attachments and traumatic tip according to the principles of the present teachings.

According to the principles of the present teachings, elongation system 14 can comprise any one of a number of actuation methods, including hydraulic, pneumatic, electric motor, ratchets driven by shape memory alloy wires, and manual pushing. FIG. 2 illustrates a device wherein the two balloons 26, distal and proximal, are each mounted to concentric inner and outer catheters, respectively, where the inner catheter can be manually pushed forward relative to the outer catheter, increasing the distance between the two balloons. FIG. 3 illustrates a schematic of the present teachings wherein distal and proximal balloon inflation ports are connect through channels in the inner and outer catheters, respectively, to enable the injection and removal of air or fluid to inflate and deflate the balloons 26.

Atraumatic Tip

According to the principles of the present teachings, atraumatic tip 18 is employed to provide progressive tapering or reduction in the amount of stiffness along at least a portion of the length of the device 10. More particularly, the stiffness of a proximal end 36 of atraumatic tip 18 that is adjacent an end of elongation system 14 and/or fenestrated attachment system 22 is generally greater than a distal end 38 of atraumatic tip 18. In some embodiments, this stiffness reduction along the length of atraumatic tip 18 can be linear, exponential, or define a non-linear predetermined reduction. Atraumatic tip 18 can comprise one or more internal flexure members and an optional covering or sheath disposed about flexure members.

Local Delivery of Medically Relevant Liquids During Bowel Extension

As part of the bowel extension process, it may be desired to deliver and/or evacuate various forms of medication or other medically relevant substances in liquid form to the bowel lumen 100. The term "medically relevant liquid" will be used herein to denote any liquid that may be used for therapeutic and/or operational purposes that is intended to be introduced to tissue for medical therapy and/or device operation. For example, it is currently unknown whether any pain will be caused by the applied tension, but in the case that it is, local topical pain medication, such as viscous lidocaine, delivered directly to the tensioned bowel tissue would be significantly more effective and safe than systemic narcotics which are typically avoided if possible to prevent systemic side effects and tolerance. Beyond therapeutics, barium sulfate or other radiographic contrast agents could be injected into the flush port to both monitor device location and insure proper device attachment.

Furthermore, when moving the device 10 within the bowel 100 for growth, it needs to slide within the bowel 100 without bunching the newly grown bowel tissue. The attachment balloons 26, which may induce some friction drag on the bowel lumen 104 when deflated, would slide more easily with use of a lubricating medically relevant liquid delivered around the device 10. Such lubrication would also be useful to enable smooth insertion, repositioning, and removal of the device 10 from the bowel 100.

Moreover, according to the principles of the present teachings, delivery of substances around the device 10 within the bowel 100 may include the synergistic application of GLP-2, growth hormone, or even glutamine (a well-known enterocyte fuel) to improved bowel growth in combination with bowel stretching. GLP-2 (Gattex™) delivered systemically, has been demonstrated to increase bowel length in short bowel patients. Unfortunately, while systemic delivery is effective at inducing some bowel growth, it has significant side effects including nausea, vomiting, bloating, headache, and irritation at the subcutaneous injection site. Moreover, it is also very expensive, costing $300,000 a year per patient treated.

However, according to the present teachings, any one or more medically relevant liquids can be used: local pain and/or inflammatory medication, such as low dose lidocaine, acetaminophen (Tylenol), ibuprofen (Motrin), and the like; growth factors, such as Teduglutide/GLP2 (Gattex); locally applied steroids, such as budesonide for inflammatory bowel disease use; local applied chemotherapy, such as for small bowel tumors; and any liquid enteral medication, such as a jejunostomy tube. In some embodiments, evacuation of the medically relevant liquid may be beneficial, such as when employing steroids or chemotherapeutic agents.

It has previously been demonstrated that GLP-2, applied systemically in conjunction with mechanotransductive treatment using osmotic pressure to inflate the bowel, creating tension on the bowel wall (without the use of a specific device), has a synergistic effect, where the growth factor enhances the mechanotransductive action such that the combination would induce more growth than either separately. Using a bowel extender device in conjunction with systemic application GLP-2 would have such a synergistic effect. To mitigate the side effects and injection site problems with the systemic use of GLP-2, GLP-2 can be solely delivered locally to the tensioned bowel tissue, reducing the overall effects on the rest of the body and reducing the total amount of growth factor required.

Device Features and Use for Local Delivery of Medical Liquids

All of these potential applications call for the delivery of medical substances in liquid form locally to the bowel tissue 100 surrounding the bowel extender device 10. To this end, as illustrated in FIGS. 4 and 5A-5C, device 10 can comprise medically relevant liquid delivery system 16 having an injection line 50 extending through at least one expanding device 26 to one or more ports 52 disposed between expanding devices 26 according to some embodiments. Ports 52 can be in fluid communication with a volume 200 (FIG. 5A) formed within bowel 100 defined by bowel lumen 104 and expanding devices 26. When expanding devices 26 are in the inflated position whereby they engage, contact, and generally seal against lumen 104, volume 200 is a contained volume to which medically relevant liquid can be introduced from a source external to the body through injection line 50 and one or more ports 52 thereto. In this way, medically relevant liquids are introduced and contained at a treatment location for direct treatment. Injection line 50, being internal to device 10, provides unobstructed access to volume 200 without requiring a separate line to be introduced in a space between expanding device 26 and lumen 104, which would result in reduced contact between expanding device 26 and lumen 104 negatively effecting mechanotransductive treatment.

In some embodiments, injection line 50 can extend along a length of catheter structure 20 and be operably coupled to a fluid system 60, such as a fluid source 62, pump 64, distribution manifold 66, and/or syringe 68, through which fluids and medically relevant liquids can be delivered. In this way, introduction of medically relevant liquid can be automated (via pump 64 and distribution manifold 66) and/or manual (via syringe 68).

In some embodiments, injection ports 52 can be disposed at a plurality of positions along device 10. More particularly, in some embodiments, ports 52 can be disposed along linear positions generally equidistant between expanding devices 26. In some embodiments, ports 52 can be radially disposed about device 10 to facilitate even application of medically relevant liquid within volume 200. It should be noted that in some embodiments, ports 52 can be disposed to outboard locations relative to expanding devices 26—that is, positions not within volume 200—to facilitate movement of device 10 within bowel 100. In some embodiments, balloon 26 is a toroidal structure that is fixed outside the catheter 20 and the injection line 50 runs completely under the balloon 26 to the end of the catheter 20 and out end caps formed on ends of balloon 26. It should be understood that injection line 50 can be disposed in any one of a number of configurations, including but not limited to through an inner portion of catheter 20 (see FIGS. 4 and 5A-5C), through an outer portion of catheter 20, or between several catheters of catheter structure 20.

Thus, when medically relevant liquid is injected into an exterior injection port, it will emanate from the multiple corresponding exit ports and come into contact with the interior of the bowel lumen surrounding the device. In this manner, medically relevant liquids can be delivered directly to the bowel tissue surrounding the device. This delivery of medically relevant liquids is independent of the state of operation of the extender device, and can be accomplished both while the device is applying tension to the bowel and while it is not.

In addition, it may be desired to enhance the even application of the medically relevant liquids to the bowel tissue and to improve the absorption of the medically relevant liquids into the tissue. This can be accomplished through the use of the bowel extender to mechanically spread the medically relevant liquid and rub it into the tissue by alternately extending and retracting the bowel extender device with the balloon attachments deflated such that the deflated attachment portions of the device slide back and forth within the bowel lumen evenly distributing the applied medically relevant liquid to the tissue.

These features also provide the ability to remove or evacuate medically relevant liquids and other materials from the bowel through the same channels. This could be useful for relieving pressure caused by possible bowel occlusion induced by the presence of the device.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A mechanotransductive bowel extender device comprising:
    an elongation system being operable to apply a tensile force to a bowel of a patient, the tensile force being configured to encourage growth of the bowel through mechanotransductive treatment;
    an engagement system having a pair of attachment mechanisms disposed on opposing ends of the elongation system, said pair of attachment mechanisms being configured to couple to the bowel and transmit the tensile force to the bowel; and
    a liquid delivery system operably coupled with the elongation system to locally apply a medically relevant liquid to the bowel, the medically relevant liquid comprises an operational liquid configured to facilitate device operation.

2. The mechanotransductive bowel extender device according to claim 1 wherein the pair of attachment mechanisms comprises a pair of spaced apart expanding devices, each of the pair of expanding devices being positionable between an expanded position and a retracted position.

3. The mechanotransductive bowel extender device according to claim 2 wherein each of the pair of expanding devices operably engaging the bowel in the expanded position and being spaced apart from the bowel in the retracted position.

4. The mechanotransductive bowel extender device according to claim 1 wherein the pair of attachment mechanisms comprises a pair of spaced apart expanding devices configured to sealingly engage the bowel in the expanded position.

5. The mechanotransductive bowel extender device according to claim 1 wherein the liquid delivery system is configured to deliver the medically relevant liquid to a volume formed between the pair of attachment mechanism and the bowel.

6. The mechanotransductive bowel extender device according to claim 1 wherein the liquid delivery system comprises an injection line fluidly coupled with at least one injection port, the at least one injection port outputting the medically relevant liquid.

7. The mechanotransductive bowel extender device according to claim 6 wherein the at least one injection port is positioned between the pair of attachment mechanisms of the engagement system.

8. The mechanotransductive bowel extender device according to claim 6 wherein the at least one injection port comprises a plurality of injection ports positioned between the pair of attachment mechanisms of the engagement system.

9. The mechanotransductive bowel extender device according to claim 6 wherein the at least one injection port comprises a plurality of injection ports radially positioned about the elongation system between the pair of attachment mechanisms of the engagement system.

10. The mechanotransductive bowel extender device according to claim 6, further comprising: a catheter structure extending from the elongation system, the injection line of the liquid delivery system extending through the catheter structure.

11. The mechanotransductive bowel extender device according to claim 1 wherein the medically relevant liquid comprises a therapeutic liquid for medical therapy.

12. The mechanotransductive bowel extender device according to claim 1 wherein the medically relevant liquid comprises a local topical pain medication.

13. The mechanotransductive bowel extender device according to claim 1 wherein the medically relevant liquid comprises a radiographic contrast agent for monitoring a location or operation of the mechanotransductive bowel extender device.

14. A method of mechanotransductive bowel extension comprising:
providing an elongated body within a bowel of a patient, the elongated body having a pair of attachment mechanisms disposed on opposing ends of the elongated body; coupling the pair of attachment mechanisms to the bowel;
actuating the elongated body to apply a tensile force to the bowel, the tensile force being sufficient to encourage growth of the bowel; and
applying medically relevant liquid to the bowel via the elongated body, the medically relevant liquid further facilitating device operation.

15. The method according to claim 14 wherein the coupling the pair of attachment mechanisms to the bowel comprises actuating an expanding device to sealingly engage the bowel.

16. The method according to claim 14 wherein the locally applying medically relevant liquid comprises locally applying medically relevant liquid within a volume between the pair of attachment mechanisms.

17. The method according to claim 14 wherein the locally applying medically relevant liquid comprises locally applying a therapeutic liquid for medical therapy.

18. The method according to claim 14 wherein the locally applying medically relevant liquid comprises locally applying an operation liquid to facilitate device operation.

19. The method according to claim 14 wherein the locally applying medically relevant liquid comprises locally applying a radiographic contrast agent.

* * * * *